United States Patent [19]

Bieri

[11] Patent Number: 5,173,738
[45] Date of Patent: Dec. 22, 1992

[54] DEVICE FOR INSPECTING CONTACT LENSES

[76] Inventor: Fritz Bieri, Johannisbergstrasse 69, CH 8645 Jona, Switzerland

[21] Appl. No.: 499,360

[22] PCT Filed: Sep. 1, 1989

[86] PCT No.: PCT/CH89/00159

§ 371 Date: May 7, 1990

§ 102(e) Date: May 7, 1990

[87] PCT Pub. No.: WO90/02535

PCT Pub. Date: Mar. 22, 1990

[30] Foreign Application Priority Data

Sep. 7, 1988 [CH] Switzerland .................. 3350/88

[51] Int. Cl.⁵ .................. G01B 9/00; G01N 21/00
[52] U.S. Cl. .................. 356/124; 356/239
[58] Field of Search .................. 356/124–127, 356/244, 246, 237, 239; 206/5.1; 220/663; 350/23.9; 359/804

[56] References Cited

U.S. PATENT DOCUMENTS

| | | | |
|---|---|---|---|
| 1,988,169 | 1/1935 | Duckwall | 356/239 |
| 3,029,694 | 4/1962 | Dantzic | 350/239 |
| 3,981,593 | 9/1976 | Boyle | 356/239 |
| 4,002,234 | 1/1977 | Loshaek . | |
| 4,232,966 | 11/1980 | Schpak et al. | 356/124 |
| 4,297,032 | 10/1981 | Temple | 356/239 |
| 4,392,569 | 7/1983 | Shoup . | |
| 4,395,120 | 7/1983 | Takahashi | 356/125 |
| 4,415,076 | 11/1983 | Campbell | 356/124 |
| 4,520,923 | 6/1985 | Waldman . | |
| 4,545,479 | 10/1985 | Figari . | |
| 4,796,991 | 1/1989 | Gordon et al. | 356/125 |

FOREIGN PATENT DOCUMENTS 2093605 9/1982 United Kingdom .

OTHER PUBLICATIONS

Contactologia "a device for Examining Contact Lenses at the Slit lamp" vol. 11, No. 4, Dec. 1989, F. Bieri.
The New England Journal of Medicine vol. 321, No. 12, Sep. 1989, Schein et al, pp. 773–778 and 779–783.
"Contact lenses" Jan./Mar. 1982 Soft Contact Lens Cleaning: a scanning Electron Microscopic Study Hesse et al.

Primary Examiner—Richard A. Rosenberger
Assistant Examiner—Hoa Q. Pham
Attorney, Agent, or Firm—Frishauf, Holtz, Goodman & Woodward

[57] ABSTRACT

The device is useful for detecting deposits on the surface of contact lenses and changes in the material of the contact lenses. It consists of an optically transparent rod-shaped body (1) with two end faces. One end face (2), in which the contact lens is placed, has a smooth surface and can be spherical, aspherical or toroidal, with a curvature in the range of that of the contact lens to be examined. The other end face (3) has a smooth or mat surface and can be flat, convex or concave. The rod-shaped body (1) may also be assembled from elements (4, 8, 11). The device is cheap to manufacture and simple for occulists, opticians and wearers of contact lenses to use.

18 Claims, 1 Drawing Sheet

DEVICE FOR INSPECTING CONTACT LENSES

FIELD OF THE INVENTION

The invention relates to a device for inspecting contact lenses which enables the verification of deposits on the surface and changes in the material of the contact lenses.

BACKGROUND

As is known, organic and inorganic deposits are formed on the surfaces of the contact lenses, and microorganisms as well as fungi also collect there. The organic deposits are parts of the lacrimal fluid such as proteins, mucines and lipids. The inorganic deposits (metal, iron, rust) are due to environmental conditions (air pollution, road dust, metal abrasives). Additional inorganic deposits are those of calcium salts which are also called hard water deposits. They are formed when flushing the lenses with tap water or due to a change of the pH value of the lacrimal fluid, e.g. due to medicaments or physiological influences. The microorganisms (bacteria, virus) and fungi belong to the normal microflora of the conjuctiva, the conjuctive sac and the lacrimal ducts. The normal microflora change as soon as the balance of the microflora becomes disturbed, be it due to germ transfer via the hands, improper cleaning and desinfection, illness or metabolic disturbances (diabetic) of the lens wearer or due to contact of the lenses with the environment. In addition it is known that the contact lenses, in the course of their use, are subjected to changes, such as changes and damage of their material. The changes of the material, e.g. discolorations, are based on environmental influences, e.g. cigarette smoke, colored vapors, cosmetics, or stains transferred from storage containers. Damage may be in form of hairline cracks, abrasions, scratches, marginal fractures or breaks, and due to improper handling of the contact lenses.

These changes of the contact lenses listed above result in various complications for the user or wearer such as e.g. an intolerability against the contact lenses so that they cannot be worn anymore. Also acute medical conditions, such as development of diseases by infection (to be observed particularly on lenses worn during extended periods) or chronic irritations as a gigantopapillary conjuctivitis, can be observed; they are somewhat less numerous but are at the center of medical treatments. Since the contact lenses are subjected to many influences adversely affecting their wearing quality and optical characteristics, regular inspections by the person adapting them (ophthalmologist, optician) to the wearer as well as by the wearer must be provided. Each wearer of contact lenses is instructed to clean them daily if possible. The sooner the cleaning is effected, the greater is the success. Various cleaning methods are in use such as e.g. chemical, thermic, encymatic, mechanical or ultrasonic treatments. In order to carry out the inspection, use of the following methods is made:

Contact lens viewing on the eye with a slit lamp (binocular microscope);

contact lens viewing with the lens held on the finger or placed in a transparent container filled with fluid, by using the naked eye and the slit lamp;

contact lens viewing in black field illumination by using a binocular microscope.

Such inspections are complicated, can only be carried out by the ophthalmologist or optician or they provide insufficient information.

THE INVENTION

It is an object to overcome these deficiencies and to provide a simple inspection device that can be used by an ophthalmologist r by an optician, as well as by the user with ease and without any effort.

Briefly, the contact lenses can be checked for clarity, integrity, and absence of deposits by placing them on a rod-shaped body, for example of about 10 cm length and 3 cm diameter, which can be circular, elliptical or polygonal in cross section, and is made of transparent, essentially noncompressible material, for example of plastic. The body has a first optical end surface curved to receive the contact lens to be inspected, so that the contact lens can be placed thereon; and a second optical end surface which can be used either for viewing, or for transmitting light through the plastic body and through the contact lens, for ease of visibility. The surface on which the contact lens is placed can be spherical, toroidal, aspherical, and the other end surface can be flat, convex or concave. The surfaces can be shiny or glossy or matte or frosted, in dependence on intended use with light, which can be ambient illumination or a separate light source.

DRAWINGS

The invention will now be explained by a detailed description of various embodiments and by referring to the drawings wherein.

DETAILED DESCRIPTION

Figure 1:
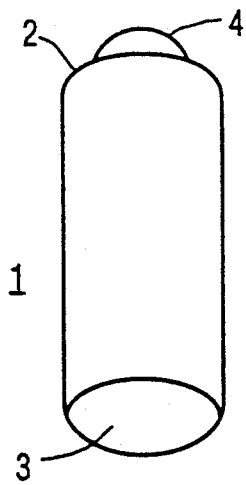
FIG. 1 is an isometric view of a rod-shaped body made of a transparent material.

FIG. 1 illustrates a transparent, essentially noncompressible body 1 having a smooth surface of e.g. acrylic glass, e.g. Plexiglass (Trademark). One end surface 2 of this body is spherical, aspherical or of toroidal shape. The other end surface 3 is shown to be plan, of flat; it may be concave, or convex, however. The contact lens L to be inspected is laid on the first, in FIG. 1 the top surface 2. The contact lens will adhere on end surface 2 due to the curvature of that surface. This curvature preferably is formed by several curved areas generated by different radii of curvature. These radii are within the range of from 7 to 10.5 millimeters. The curvature matches the curvatures of the commercially available contact lenses. Contact lenses made of hydrophilic or highly hydrophilic material are preferably laid onto the central zone of end surface 2 in the vicinity of the longitudinal axis of body 1. Contact lenses made of gas-permeable material are preferably laid on the marginal zone of end surface 2. In particular cases the adhesion of the contact lenses may be increased by applying a liquid onto end surface 2. The other end surface 3 is ground even and frosted, or mat.

Checking a contact lens:

The contact lens L arranged on the spherical end surface 2 can be viewed in two ways:

(1) In normal bright surroundings the contact lens is viewed against a dark background. Thus only the contact lens is illuminated.

(2) The mat end surface 3 is directed toward a light source so that the contact lens L is illuminated in light transmitted by body 1. Light is thus transmitted into the second end surface 3, through the body 1, to and through the first curved end surface 2 and through Lens L. The light source which may be the daylight, a slit lamp or a light diode 5 (FIG. 5), is not seen as such by the user. One sees only an evenly bright surface. The viewer may use a reading glass for magnifying the image of the contact lens.

Figure 3:
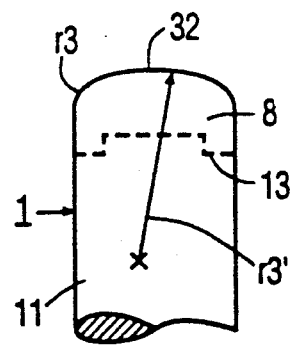
Figure 5:
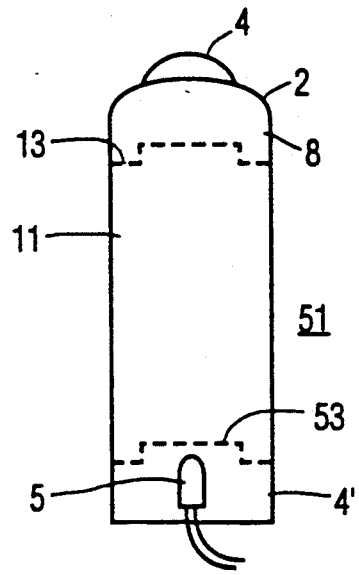
FIG. 5 depicts a shape of the other end surface of the rod-shaped body composed of assembled elements.
Figure 7:
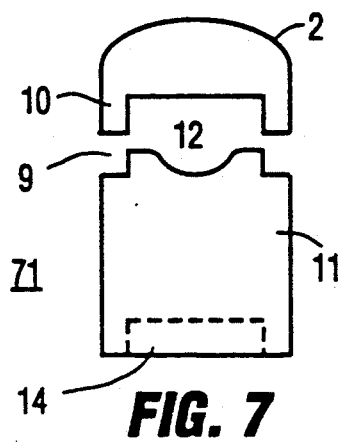
FIG. 7 illustrates a rod-shaped body with a recess.

In FIG. 1, transparent body 1 is shown to be of cylindrical shape with circular cross section. Of course it may be rod-shaped having an elliptic or polygonal (e.g. hexagonal) cross section. The rod-shaped body of elliptic or polygonal shape is better for the user with regard to its handling. The body need not consist of one piece. It may also be assembled from pushed-together elements such as shown in FIGS. 3, 5 and 7. A plug-type connection has proved to be easy and comfortable in use, and simple to manufacture. Basically other connections are also possible.

Figure 2:
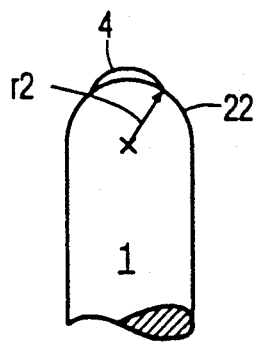
FIGS. 2 to 4 show various curvatures of one end surface of the rod-shaped body which receives the contact lenses.
Figure 4:
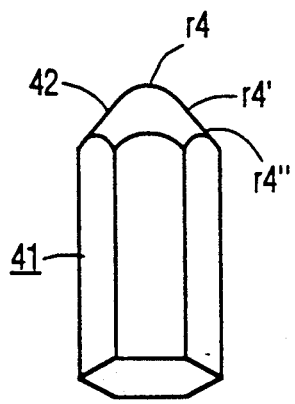

FIGS. 2, 3 and 4 show embodiments with spherical end surfaces 2 having different curvatures. These surfaces are excellent for a perfect support of hydrophilic or gas-permeable contact lenses. In particular when using soft contact lenses, care must be taken that they rest on end surface 2 without folds being formed. The shapes of the different end surfaces are approximately comparable to the surface of the eyeball. They may be ground spherically, toroidally or aspherically.

FIG. 2 shows a curvature of end surface 22 having single radius of curvature r2. FIG. 3 illustrates an end surface 32 having a curvature that is composed of two different radii of curvature r3 and r3'. Lens L has been omitted from FIG. 3 for clarity. In addition, FIG. 3 shows the possibility of assembling body 1 of different elements; e.g. an element 8 having the end surface of the required composite curvature with radii r3 and r3' may be joined with a base body element 11. The coupling is represented as a plug-type connection.

The body 1 of FIGS. 2 and 3 is shown to have circular cross section. Elliptic or polygonal cross sections may also be used.

FIG. 4 shows an end surface 42 whose curvature is composed of several radii of curvature r4, r4', r4''. In addition, the body 41 as illustrated in FIG. 4, has hexagonal cross section. Here too, the body 41 can be constituted by several elements.

FIG. 5 shows transparent body 51 with a smooth surface and with a matte or frosted end surface 53. A holder 4 is attached to end surface 53, receiving an incandescent bulb or a light diode 5 which is fed by a battery on site or by the standard current supply. This embodiment makes the user (ophthalmologist, optician, wearer) independent of other light sources. Holder 4, as an element, may be attached to a unitary body or to body element 11 of composite body 51. If a unitary body is used, the matte end surface is flat like end surface 3 and the mating end surface of the holder 4 also is even or flat; the surfaces are connected to each other, e.g. by an adhesive. If the body is a composite, the matte or frosted end surface 53 and the matching end surface of the holder 4 are formed as a plug-in connection as indicated by dashed lines. Alternatively, end surface 53 may be smooth or clear and the matching surface of holder 4 matte or frosted. Providing a clear transparent surface 53 on body element 11 and a frosted diffusing surface on element 4 is of particular advantage if the contact lens lying on end surface 2 is viewed in transmitted light either with light source 5 or, upon removal of holder 4, with light falling directly on smooth, clear surface 53. Body 51 can be assembled of the respective elements 4, 8 and 11. Element 8 is formed and selected to have the desired curvature at surface 2 for the lens L.

Figure 6:
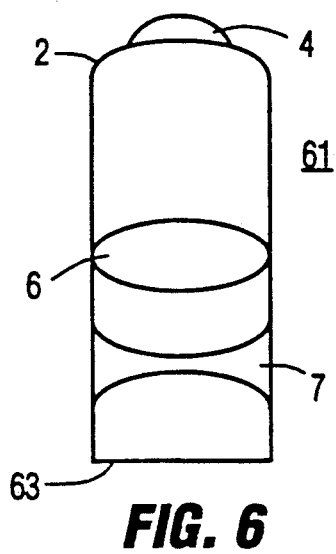
FIG. 6 depicts a further embodiment of the rod-shaped body with its two end surfaces.

FIG. 6 shows transparent body 61 with a smooth surface. A convex lens 6 is integrated into the body. Surface 2 receiving lens L is smooth and clear. The lens 6 may be arranged in body 61 as illustrated or in a body element 11 as in FIGS. 3 and 5 (not shown in FIG. 6), and in such case the respective elements are assembled as needed. The flat surface 63 is not frosted, but clear and smooth. The contact lens L supported by spherical end surface 2 is so viewed that the smooth end surface 63 is placed close or proximate to the eye of the viewer and the spherical end surface with the contact lens L thereon remote or distal from the viewer. The lens L on surface 2 is held against a dark background. Convex lens 6 acts as a magnifying glass and magnifies the image of the contact lens. Convex lens 6 is placed within transparent body 61 in such a way that it generates a real or virtual, magnified image of the contact lens L on spherical end surface 2. The kind of image obtained depends upon whether the distance between convex lens 6 and end surface 2 is greater or smaller than the focal lengths of the convex lens 6. Convex lens 6 may be adhered onto the correspondingly formed end surface 3 so that there is no space between them. The material of the convex lens 6 which may consist of a gaseous, liquid or solid medium must have a refractive index which differs from that of the material of body 1.

There exists also the possibility of providing a dispersing lens 7 as illustrated in FIG. 6 together with a convex lens 6 within rod-shaped body 1 or adhering it directly onto correspondingly formed end surface 63 without any space inbetween. Here too, end surface 63 is proximate to the eye of the viewer, i.e. it is closer to the eye than end surface 2 with the contact lens L. Lens L is held against a dark background. The medium of dispersing lens 7 has another refractive index than has the material of body 61 and may be of gaseous, liquid or solid form, such as air, water or another type of glass. The distance between the two lenses 6, 7 is selected such that the image of the contact lens L on end surface 2 which is generated by convex lens 6 lies between the focal length and the double-focal length of dispersing lens 7, thus generating a magnified virtual image for the viewer of the contact lens. The additional dispersing lens 7 has the advantage that the limitation of the image aperture which is usual on convex lenses having high dioptric values is eliminated.

Convex lens 6 and dispersing lens 7 may be fixed within rod-shaped body 61 or provided within elements not shown in FIG. 6. which can be stacked or plugged together for assembly. In both cases magnified images of the contact lens will be obtained. Rod-shaped body 61 of FIG. 6 or the elements may be of circular., elliptic or polygonal cross-section. Instead of the lenses, a magnifying optical system may be provided.

FIG. 7 shows rod-shaped body 71 which is assembled from several elements, only two being shown. Element 10 comprises, as on the previous embodiments of the invention, the one end surface 2 and a plug-in or screw plug connection 9. In FIG. 7, surface 2 is shown spherical, so that in FIG. 7, the side view representation is circular with a single radius of curvature. Element 10 is designed as a cover and provides, together with a suitably shaped cavity in body element 11, a hollow space or recess 12. The upper side of space 12 is flat. Only a single contact lens can be stored in recess 12. The lens is firmly held in position. Storage within closed hollow space 12 having further a storage liquid therein is advantageous both for soft and hard contact lenses because they cannot dry out and thus cannot be destroyed. A screw or plug-in recess 14 is formed in the lower end of body element 11 for an additional element which may be a holder 4 with a light source 5 (FIG. 5) or a lens member (FIG. 6). The body represented in FIG. 7 can be used as a storage case for a contact lens. For a pair of contact lenses, two bodies are required which may be either independent of each other or connected to each other by means of a holding arrangement. This holding arrangement may either be a snap-in arrangement into which the two rod-shaped bodies 1 are snapped or may be formed as a portion integrated with the two bodies. This results in the advantage of having a combination of a contact lens storage case and of an inspection device for the lenses. FIG. 7 shows a simple plug-and-socket arrangement for coupling elements 10 and 11.

Body 1 is represented in FIGS. 1-7 as having a blank transparent side surface. Preferably its side surfaces can be colored black, thus eliminating unpleasant reflections and undesired images. If a translucent body is illuminated, for example, sideways by a light source, the contact lens on end surface 2 will be visible when placed in front of a dark background free of reflections and images.

The embodiments represented in FIGS. 1 to 7 may be used for viewing by the person adapting the lenses to a user e.g. an ophthalmologist or optician, as well as by the wearer. Preparations for viewing are fast and uncomplicated; this is an advantage since the device according to the invention is ready at hand and on most embodiments need no artificial illumination. The length of the body does not exceed 10 centimeters; its diameter is below 3 centimeters. The device according to the invention thus is small, low in weight and can easily be transported. In addition, the manufacturing costs are low. Each wearer of contact lenses is now in a position to verify the deposits and damages on the material of his contact lenses so early that their cleaning has the desired effect and complications can be avoided. This holds true particularly in cases in which the contact lens practice of an ophthalmologist or optician is not within reach or is closed,

I claim:

1. Device for inspecting contact lenses having radii of curvature within a predetermined range to determine the formation of deposits on surfaces of the contact lenses and of changes in the material of which the lenses are made,
    said device comprising
    a rod-shaped, essentially non-compressible body having a cross section of at least one of: circular shape; elliptical shape; polygonal shape,
    said device being of optically transparent material, and defining a first optical end surface and a second optical end surface,
    the first one of said end surfaces being curved, and adapted to receive the contact lens to be inspected in engagement therewith and being formed in at least one of : part-spherial shape; toroidal shape; and aspherical shape, with at least one radius of curvature which is within said predetermined range;
    the second end surface defining, selectively, a surface of at least one of: flat shape; convex shape; and concave shape to permit inspection of a lens positioned on said first end surface by light transmitted between said first end surface and said second end surface through said transparent body and hence through said contact lens positioned thereon; and
    wherein the first end surface of the body which is adapted to receive the contact lens is transparent and smooth; and
    the second end surface of said body, at least in part, is flat, and frosted or matte.

2. The device of claim 1, further including a holder element; and
    a light source coupled to said holder element, said holder element being coupled to said body and said at least part flat and frosted second end surface.

3. The device of claim 1, wherein said body includes a convex lens.

4. The device of claim 3, wherein said convex lens comprises at least one of: a gaseous medium; a liquid medium; a solid medium.

5. The device of claim 3, wherein said body further includes a dispersing or concave lens.

6. The device of claim 5, wherein at least one of said lenses includes: a gaseous medium; a liquid medium; a solid medium.

7. The device of claim 1, wherein said body includes a dispersing or concave lens.

8. The device of claim 7, wherein said concave lens comprises at least one of: a gaseous medium; a liquid medium; a solid medium.

9. The device of claim 1, wherein said body comprises a plurality of optically transparent part-elements.

10. The device of claim 9, wherein one of said part-elements is formed with said first end surface adapted to receive the contact lens to be inspected and to be engaged thereby.

11. The device of claim 9, wherein one of said elements comprises a holder element, and a light source coupled to said holder element for transmitting light into said body.

12. The device of claim 9, wherein one of said elements is formed with a recess to define, in combination with another element placed adjacent thereto, a hollow space or cavity for receiving a contact lens and, optionally, a storage liquid.

13. The device of claim 12, including a connecting arrangement for coupling said part-elements together.

14. The device of claim 13, wherein said connecting arrangement comprises a plug-and-socket connection.

15. The device of claim 1, further including a lens element interposed in said rod-shaped body between said two end surfaces.

16. Device for inspecting contact lenses having radii of curvature within a predetermined range to determine the formation of deposits on surfaces of the contact lenses and of changes in the material of which the lenses are made,
  said device comprising
    a rod-shaped, essentially non-compressible body having a cross section of at least one of: circular shape; elliptical shape; polygonal shape,
    said device being of optically transparent material, and defining a first optical end surface and a second optical end surface,
    the first one of said end surface being curved, and adapted to receive the contact lens to be inspected in engagement therewith and being formed in at least one of: part-spherial shape; toroidal shape; and aspherical shape, with at least one radius of curvature which is within said predetermined range;
    the second end surface defining, selectively, a surface of at least one of: flat shape; convex shape; and concave shape to permit inspection of a lens positioned on said first end surface by light transmitted between said first end surface and said second end surface through said transparent body and hence through said contact lens positioned thereon; and
    wherein said body and its two end surfaces comprise a single, unitary, optically transparent element.

17. The device of claim 16 further including a holder element; and
  a light source coupled to said holder element, said holder element being coupled to said body and said second end surface.

18. The device of claim 16, wherein both end surfaces of said body are transparent and smooth.

* * * * *